(12) United States Patent
Batzer et al.

(10) Patent No.: US 12,402,818 B2
(45) Date of Patent: Sep. 2, 2025

(54) SUPPRESSING ECHO EFFECTS ON ELECTRODES WHEN MEASURING BIOELECTRIC SIGNALS

(71) Applicant: Siemens Healthcare GmbH, Erlangen (DE)

(72) Inventors: Ulrich Batzer, Spardorf (DE); Matthias Brumhard, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 602 days.

(21) Appl. No.: 17/117,450

(22) Filed: Dec. 10, 2020

(65) Prior Publication Data

US 2021/0186401 A1 Jun. 24, 2021

(30) Foreign Application Priority Data

Dec. 19, 2019 (EP) .................................... 19218075

(51) Int. Cl.
*A61B 5/25* (2021.01)
*A61B 5/00* (2006.01)
(Continued)

(52) U.S. Cl.
CPC ................. *A61B 5/25* (2021.01); *A61B 5/30* (2021.01); *A61B 5/305* (2021.01); *A61B 5/72* (2013.01);
(Continued)

(58) Field of Classification Search
CPC ......... A61B 5/305; A61B 5/389; A61B 5/318; A61B 5/31; A61B 5/313; A61B 5/308;
(Continued)

(56) References Cited

U.S. PATENT DOCUMENTS

| 5,546,332 A | 8/1996 | Strobach | |
| RE37,130 E * | 4/2001 | Fiori, Jr. | H04B 3/28 330/69 |

(Continued)

FOREIGN PATENT DOCUMENTS

| CN | 101951832 A | 1/2011 |
| DE | 10353969 A1 | 7/2005 |

(Continued)

OTHER PUBLICATIONS

German Office Action dated Jul. 7, 2020.
(Continued)

*Primary Examiner* — Joanne M Rodden
*Assistant Examiner* — Matthew David Becton
(74) *Attorney, Agent, or Firm* — Harness, Dickey & Pierce, P.L.C.

(57) ABSTRACT

An interference signal measuring facility is in a differential voltage measuring system with a signal measuring circuit for measuring bioelectric signals with a number of useful signal paths, each with a sensor electrode. In an embodiment, the interference signal measuring facility has an additional sensor lead for each sensor electrode each of which is electrically connected to a ground connection of a supply lead of a sensor electrode; and a measuring amplifier circuit, for each sensor electrode connected to the additional sensor lead via an electrical resistor, configured to detect a change in electric potential occurring on the sensor lead and to determine an electrode reference interference signal therefrom. Also described is an interference signal compensation facility; a differential voltage measuring system; and a method for generation an interference-reduced biological measurement signal are described.

19 Claims, 5 Drawing Sheets

(51) Int. Cl.
  *A61B 5/30* (2021.01)
  *A61B 5/305* (2021.01)
  *A61B 5/308* (2021.01)
  *A61B 5/31* (2021.01)
  *A61B 5/313* (2021.01)
  *A61B 5/318* (2021.01)
  *A61B 5/369* (2021.01)
  *A61B 5/389* (2021.01)

(52) U.S. Cl.
  CPC .......... *A61B 5/7203* (2013.01); *A61B 5/7225* (2013.01); *A61B 5/725* (2013.01); *A61B 5/7278* (2013.01); *A61B 5/308* (2021.01); *A61B 5/31* (2021.01); *A61B 5/313* (2021.01); *A61B 5/318* (2021.01); *A61B 5/369* (2021.01); *A61B 5/389* (2021.01); *A61B 5/7221* (2013.01); *A61B 2562/182* (2013.01); *A61B 2562/222* (2013.01)

(58) Field of Classification Search
  CPC ..... A61B 5/369; A61B 5/7214; A61B 5/7217; A61B 5/30; A61B 5/72; A61B 5/7203; A61B 5/7221; A61B 5/25; A61B 5/7225; A61B 5/725; A61B 2562/182
  USPC .................................................. 600/547, 372
  See application file for complete search history.

(56) References Cited

U.S. PATENT DOCUMENTS

| | | | |
|---|---|---|---|
| 7,993,167 | B2 | 8/2011 | Keightley et al. |
| 2003/0163170 | A1* | 8/2003 | Faisandier ............. A61B 5/276 607/27 |
| 2008/0312523 | A1* | 12/2008 | Dunseath ............... A61B 5/369 600/383 |
| 2009/0054758 | A1 | 2/2009 | Dunseath |
| 2009/0112080 | A1* | 4/2009 | Matthews ................ A61B 5/30 600/393 |
| 2010/0145217 | A1 | 6/2010 | Otto et al. |
| 2011/0001497 | A1 | 1/2011 | Chetelat et al. |
| 2012/0157867 | A1 | 6/2012 | Pekonen |
| 2014/0081114 | A1* | 3/2014 | Shachar ................... A61B 5/24 600/378 |
| 2016/0228024 | A1 | 8/2016 | Batzer et al. |
| 2017/0099528 | A1* | 4/2017 | Batzer .................. A61B 5/7225 |
| 2018/0103907 | A1 | 4/2018 | Batzer |
| 2018/0249960 | A1 | 9/2018 | Gupta et al. |
| 2019/0353692 | A1 | 11/2019 | Batzer |
| 2020/0163577 | A1* | 5/2020 | Chen ........................ A61B 5/30 |
| 2020/0297282 | A1 | 9/2020 | Batzer |

FOREIGN PATENT DOCUMENTS

| | | |
|---|---|---|
| DE | 102014214994 A1 | 2/2016 |
| DE | 102015202447 A1 | 8/2016 |
| DE | 102016226197 A1 | 6/2018 |
| DE | 102017214862 A1 | 2/2019 |
| DE | 102019203627 A1 | 9/2020 |
| EP | 3569143 A1 | 11/2019 |

OTHER PUBLICATIONS

Wu Xiaowei:; "Design and Application of Surface Diaphragmatic EMG Measuring System" Jan. 25, 2013; Computer Measurement and Control; Nr. 01.

Hao Hongwei et al.;"Method and Instrument for ECG Measurement Based on Two Electrodes"; Oct. 15, 2007; Space Medicine and Medical Engineering, Nr. 05.

\* cited by examiner

SUPPRESSING ECHO EFFECTS ON ELECTRODES WHEN MEASURING BIOELECTRIC SIGNALS

PRIORITY STATEMENT

The present application hereby claims priority under 35 U.S.C. § 119 to European patent application number EP19218075.0 filed Dec. 19, 2019, the entire contents of which are hereby incorporated herein by reference.

FIELD

An example embodiment of the application generally relates to an interference signal measuring facility in a differential voltage measuring system with a signal measuring circuit for measuring bioelectric signals with a number of useful signal paths each with a sensor electrode. An example embodiment of the application furthermore generally relates to an interference signal compensation facility. An example embodiment of the application moreover generally relates to a differential voltage measuring system. An example embodiment of the application also relates to a method for generating an interference-reduced biological measurement signal.

BACKGROUND

Voltage measuring systems, in particular differential voltage measuring systems, for measuring bioelectric signals are, for example, used in medicine for measuring electrocardiograms (EKGs), electroencephalograms (EEGs) or electromyograms (EMGs). With such applications, preferably a high input impedance of at least several MOhm should be observed on each measuring channel in order to reduce, or at least not amplify, the influence of interferences. The high input impedance desired should also be maintained in the cables of the aforementioned devices for measuring bioelectric signals. The measuring leads of the cables are usually surrounded by a shield. To achieve better handling, the cables are moreover flexible, narrow and light. However, these features create a conflict between the service life and handling of the cables and increase the risk of a cable defect.

One type of interferences that can occur when measuring bioelectric signals is interference signals which are coupled to the patient or into the cables or the electrodes or are present thereon. These interference signals comprise, for example, ambient electromagnetic fields, electrostatic charges and the like.

When an electric field is coupled into the electrodes, the coupled current is discharged via the body and further via the EKG component to ground and causes an interference voltage when passing through the contact electrode.

U.S. Pat. No. 7,993,167 B2 describes a method with which a shield is to prevent interference signals formed by the coupling of electric fields onto electrodes.

SUMMARY

However, the inventors have discovered that a shield of this kind has the drawback that it is only able to prevent a part of the coupling-in since there is a gap between a shield of this kind and the skin of a patient at several points and thus interferences can be coupled in between the body and the electrode shield.

At least one embodiment of the present invention is designed to reduce, or even avoid, interferences when measuring bioelectric signals acting on the electrodes.

Embodiments are directed to an interference signal measuring facility; an interference signal compensation facility; a differential voltage measuring system; and a method for generating an interference-reduced biological measurement signal.

The interference signal measuring facility according to an embodiment of the invention serves to measure interference signals on useful signal paths in a differential voltage measuring system with a signal measuring circuit for measuring bioelectric signals with a number of useful signal paths each with a sensor electrode. The interference signal measuring facility comprises an additional sensor lead for each sensor electrode which is electrically connected to a ground connection of a supply lead of a sensor electrode. Another part of the interference signal measuring facility is a measuring amplifier circuit for each sensor electrode, which is connected to the additional sensor lead via an electrical resistor and is configured to detect a change in electric potential occurring on the sensor lead and to determine an electrode reference interference signal therefrom.

The interference signal compensation facility according to an embodiment of the invention has the interference signal measuring facility according to an embodiment of the invention. The interference signal compensation facility according to an embodiment of the invention furthermore comprises an evaluation unit. The evaluation unit comprises a first adaptive filter unit configured to generate a first interference-reduced measurement signal based on a measurement signal and a reference common-mode interference signal.

The differential voltage measuring system according to an embodiment of the invention has at least one first electrode and one second electrode for measuring bioelectric measurement signals. The differential voltage measuring system according to an embodiment of the invention furthermore has at least one third electrode for potential equalization between a measurement object and the differential voltage measuring system. This third electrode can also generate the aforementioned reference common-mode interference signal. The differential voltage measuring system according to an embodiment of the invention moreover has a measuring facility. The measuring facility has a signal measuring circuit for measuring the bioelectric signals. The measuring facility furthermore also has a reference-signal unit which generates the aforementioned reference common-mode interference signal and for this purpose is connected to both the aforementioned third electrode and the signal measuring circuit.

The differential voltage measuring system according to an embodiment of the invention also has the interference signal measuring facility according to an embodiment of the invention. The differential voltage measuring system according to an embodiment of the invention shares the advantages of the interference signal compensation facility according to an embodiment of the invention and the interference signal measuring facility according to an embodiment of the invention.

The method according to an embodiment of the invention for generating an interference-reduced biological measurement signal is used to detect a possibly interference-afflicted measurement signal. Moreover, an electrode reference interference signal is detected via a measuring amplifier circuit for each sensor electrode. The respective measuring amplifier circuit is connected to the additional sensor lead via an electrical resistor and is configured to detect a change in electric potential occurring on the sensor lead and to determine an electrode reference interference signal therefrom. A reference common-mode-interference signal is also detected. A first interference-reduced measurement signal is determined based on the measurement signal and the reference common-mode interference signal.

Furthermore, an adapted reference electrode interference signal reduced by common-mode interference is determined based on the electrode reference interference signal determined by the interference signal measuring facility and the reference common-mode interference signal. Finally, a second interference-reduced measurement signal is determined based on the first interference-reduced measurement signal and the adapted reference electrode interference signal. The method according to an embodiment of the invention for generating an interference-reduced biological measurement signal shares the advantages of the interference signal compensation facility according to an embodiment of the invention and the interference signal measuring facility according to an embodiment of the invention.

A large proportion of the aforementioned components of the interference signal compensation facility according to an embodiment of the invention, in particular the evaluation unit, can be wholly or partially implemented in the form of software modules in a processor of a corresponding voltage measuring system. An extensively software-based implementation has the advantage that it is also possible to retrofit voltage measuring systems used to date in a simple way via a software update and adding the necessary hardware components, such as, for example, additional sensor leads and measuring amplifier circuits in order to work in the manner according to an embodiment of the invention.

In this regard, an embodiment is also directed to a corresponding computer program product with a computer program which can be loaded directly into a storage facility of a voltage measuring system with program sections for carrying out all the steps of the method according to an embodiment of the invention when the program is executed in the voltage measuring system. In addition to the computer program, a computer program product of this kind can optionally comprise additional parts such as, for example, documentation and/or additional components and also hardware components, such as, for example, hardware keys (dongles etc.) for using the software.

At least one embodiment is directed to an interference signal measuring facility for a differential voltage measuring system including a signal measuring circuit for measuring bioelectric signals with a number of useful signal paths, each of the useful signal paths respectively including a sensor electrode, the interference signal measuring facility comprising:
  additional sensor leads, each additional sensor lead including an additional sensor lead for each respective sensor electrode, each of the additional sensor leads being electrically connected to a ground connection of a supply lead of a respective sensor electrode;
  measuring amplifier circuits, each measuring amplifier circuit
    respectively corresponding to each respective sensor electrode
    being connected to a respective additional sensor lead via an electrical resistor
    being configured to detect a change in electric potential occurring on the respective sensor lead, and
    being configured to determine an electrode reference interference signal from the change in electric potential detected.

At least one embodiment is directed to a differential voltage measuring system, comprising:
  at least one first electrode and one second electrode for measuring bioelectric measurement signals;
  at least one third electrode for potential equalization between a measurement object and the differential voltage measuring system; and
  a measuring facility including
    a signal measuring circuit to measure the bioelectric signals,
    a reference-signal unit to detect a reference common-mode interference signal, and
    the interference signal measuring facility of an embodiment.

At least one embodiment is directed to an interference signal compensation facility, comprising:
  the interference signal measuring facility of an embodiment; and
  an evaluation unit including
    a first adaptive filter unit, configured to generate a first interference-reduced measurement signal based on a measurement signal and a reference common-mode interference signal,
    a second adaptive filter unit, configured to generate an adapted reference electrode interference signal reduced by common-mode interferences based on the electrode reference interference signal determined by the interference signal measuring facility and the reference common-mode interference signal, and
    a third adaptive filter unit, arranged downstream of the first adaptive filter unit and the second adaptive filter unit, configured to determine a second interference-reduced measurement signal based on the first interference-reduced measurement signal and the adapted reference electrode interference signal.

At least one embodiment is directed to a method for generating an interference-reduced biological measurement signal, the method comprising:
  detecting a possibly interference-afflicted measurement signal;
  detecting an electrode reference interference signal via a measuring amplifier circuit, for each sensor electrode of a plurality of sensor electrodes, each sensor electrode being respectively connected to a respective additional sensor lead via an electrical resistor and being configured to detect a change in electric potential occurring on a respective sensor lead of the respective sensor electrode and being configured to determine an electrode reference interference signal from the change in electric potential detected;
  detecting a reference common-mode-interference signal;
  generating a first interference-reduced measurement signal based on a measurement signal and the reference common-mode interference signal;
  generating an adapted reference electrode interference signal, reduced by common-mode interferences based on the electrode reference interference signal determined by the interference signal measuring facility and the reference common-mode interference signal; and
  generating a second interference-reduced measurement signal based on the first interference-reduced measurement signal and the adapted reference electrode interference signal.

At least one embodiment is directed to a non-transitory computer program product storing a computer program, directly loadable into a storage facility of a voltage measuring system, including program sections for executing the method of an embodiment when the computer program is executed in the voltage measuring system.

At least one embodiment is directed to a non-transitory computer-readable medium storing program sections, readable and executable by a computing unit, to execute the method of an embodiment when the program sections are executed by the computing unit.

BRIEF DESCRIPTION OF THE DRAWINGS

The following describes the invention again in greater detail with reference to the attached figures and with reference to example embodiments. Herein, the same components are provided with identical reference characters in the different figures. As a rule, the figures are not true to scale. The figures show.

DETAILED DESCRIPTION OF THE EXAMPLE EMBODIMENTS

Figure 1:
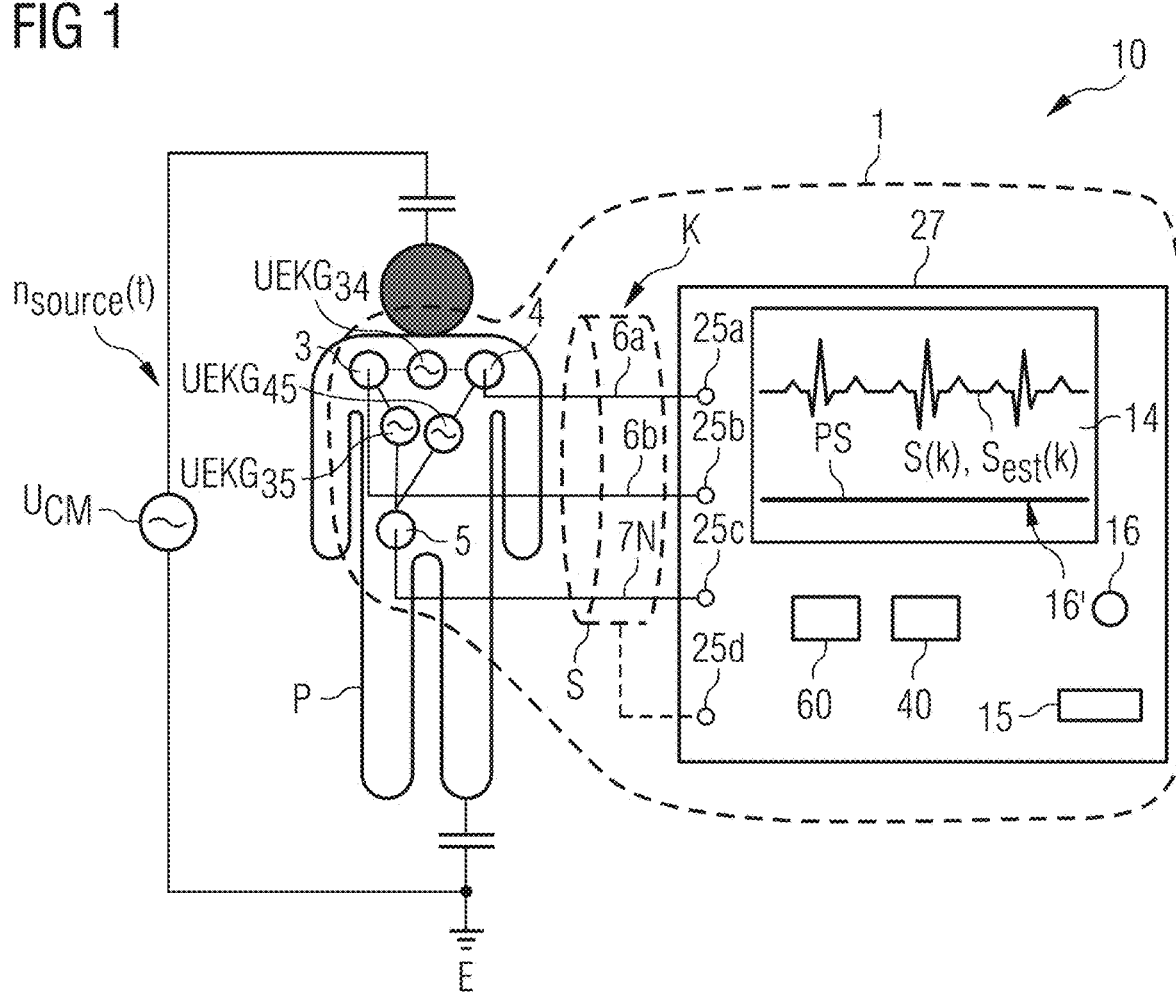
FIG. 1 a schematic example embodiment of a differential voltage measuring system including possible positioning of the electrical connectors or contacts of a on a patient, FIG. 2 a schematic view of a differential voltage measuring system with an interference signal measuring facility according to an example embodiment of the invention, FIG. 3 a schematic block diagram of an example embodiment of an interference signal evaluation unit for a differential voltage measuring system according to an embodiment of the invention, FIG. 4 a flowchart illustrating a method for generating an interference-reduced biological measurement signal according to an example embodiment of the invention, FIG. 5 a schematic view of a differential voltage measuring system with an interference signal measuring facility according to a second example embodiment of the invention, FIG. 6 a schematic block diagram of an example embodiment of an interference signal evaluation unit, FIG. 7 a schematic flowchart of an example embodiment of a method according to the invention for suppressing interference signals in a differential voltage measuring system.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above.

Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The interference signal measuring facility according to an embodiment of the invention serves to measure interference signals on useful signal paths in a differential voltage measuring system with a signal measuring circuit for measuring bioelectric signals with a number of useful signal paths each with a sensor electrode. The interference signal measuring facility comprises an additional sensor lead for each sensor electrode which is electrically connected to a ground connection of a supply lead of a sensor electrode.

Another part of the interference signal measuring facility is a measuring amplifier circuit for each sensor electrode, which is connected to the additional sensor lead via an electrical resistor and is configured to detect a change in electric potential occurring on the sensor lead and to determine an electrode reference interference signal therefrom.

As already mentioned in the introduction, the differential voltage measuring system detects bioelectric signals, for example from a human or animal patient. For this purpose, it has a number of measuring leads or useful signal paths. These connect, for example as individual cables, electrodes attached to the patient to detect the signals with the further components of the voltage measuring system, i.e. in particular the electronics used to evaluate or depict the detected signals.

The basic mode of operation of differential voltage measuring systems are known to the person skilled in the art and therefore no more detailed explanation will be given at this point. They can in particular be embodied as electrocardiograms (EKGs), electroencephalograms (EEGs) or electromyograms (EMGs).

Herein, interferences designate both interference signals, for example, couplings into the cables or via a patient, and also signal path defects, such as, for example, cable breaks, kinks or the like. Couplings-in occur during the measurement of bioelectric signals, for example EKG signals, for example frequently called common-mode interference signals or common-mode signals (CM signals).

According to an embodiment of the invention, interference signals coupled into the sensor electrodes of the differential voltage measuring system are now detected by a separate interference signal measuring facility. This advantageously enables interference signals from interference sources, such as, for example, a current-carrying cable, that primarily couple an interference signal into an electrode but hardly ever couple interference signals into the examination object's body to be measured separately.

Moreover, the separate analysis for example enables the user to be given specific handling instructions as how to remove the source of interference. The measured interference signal can also be used as an electrode reference interference signal for the targeted suppression of an interference component in the measurement signal. It is, for example, possible to use a plurality of adaptive filters for this purpose with which different interference components can be filtered out of the measurement signal.

The interference signal compensation facility according to an embodiment of the invention has the interference signal measuring facility according to an embodiment of the invention. The interference signal compensation facility according to an embodiment of the invention furthermore comprises an evaluation unit. The evaluation unit comprises a first adaptive filter unit configured to generate a first interference-reduced measurement signal based on a measurement signal and a reference common-mode interference signal. Such a reference common-mode interference signal comprises interference signals coupled into the body of the examination object. An adaptive filter unit is capable of independently changing its transmission function and its frequency during operation. Herein, an error signal is generated in dependence on an output signal from the filter and the filter coefficients are changed in dependence on the error signal such that the error signal is minimized.

Above all, the first interference-reduced measurement signal contains fewer interference signals originating from interference coupled into the body of the examination object. However, the first adaptive filter unit also reduces, albeit to a lesser extent, interference signals caused by interference coupled into the electrodes. Therefore, the electrode reference interference signal detected by the interference signal measuring facility is no longer a suitable reference for the first interference-reduced measurement signal generated by the first filter unit.

This effect is explained by the fact that every electric field in the vicinity of the patient is always coupled into the patient and electrode simultaneously. Depending on the location and nature of the interference, the degree of this varies greatly. Since the source of the interference for electrode interference and reference interference is the same electric field, depending upon the coupling, the common-mode reference measurement contains at least components of the interference on the electrode. The first adaptive filter unit now attempts to remove these identical components and as a result not only removes the common-mode interference components but also partially removes the coupling into the electrodes.

For this reason, in an embodiment the evaluation unit comprises a second adaptive filter unit with which an adapted reference electrode interference signal is generated which now only contains interference components that were not filtered out by the first adaptive filter unit. The second adaptive filter unit, which is preferably connected in parallel to the first adaptive filter unit, is configured to generate an adapted reference electrode interference signal reduced by common-mode interference based on the electrode reference interference signal determined by the interference signal measuring facility and the reference common-mode interference signal. As already mentioned, herein interference components caused by the coupling of interference fields into the electrodes but also contained in the reference common-mode interference signal are filtered out.

As already mentioned, in this way an adapted reference electrode interference signal which now only contains interference signal components that were not filtered out by the first adaptive filter unit. This adapted reference electrode interference signal can now be used as a reference signal by a third adaptive filter unit which is also part of the evaluation unit.

The third adaptive filter unit is arranged downstream of the first and second adaptive filter unit and is configured to determine a second interference-reduced measurement signal based on the first interference-reduced measurement signal and the adapted reference electrode interference signal. This second interference-reduced measurement signal is now advantageously effectively freed of both interference signals that were generated by the coupling of interference fields into the body of the examination object and of interference signals that were generated by the coupling of interference fields into the sensor electrodes of the differential voltage measuring system.

The differential voltage measuring system according to an embodiment of the invention has at least one first electrode and one second electrode for measuring bioelectric measurement signals. The differential voltage measuring system according to an embodiment of the invention furthermore has at least one third electrode for potential equalization between a measurement object and the differential voltage measuring system. This third electrode can also generate the aforementioned reference common-mode interference signal. The differential voltage measuring system according to an embodiment of the invention moreover has a measuring facility. The measuring facility has a signal measuring circuit for measuring the bioelectric signals. The measuring facility furthermore also has a reference-signal unit which generates the aforementioned reference common-mode interference signal and for this purpose is connected to both the aforementioned third electrode and the signal measuring circuit.

To measure the reference common-mode interference signal, the differential voltage measuring system has a third useful signal path with the aforementioned third electrode. In addition, the differential voltage measuring system preferably comprises a driver circuit connected between a current measuring resistor and the signal measuring circuit. The driver circuit is also called a "right-leg drive" (RLD) and is responsible for generating a signal that is regulated to the mean common-mode voltage of individual signals or all signals. This enables the aforementioned and measured common-mode interference signals in the useful signal paths to be reduced.

The third useful signal path (or "right-leg drive path") provides potential equalization between the patient and the differential voltage measuring system or the EKG measuring system. Herein, the electrode of the third useful signal path is preferably attached to the patient's right leg to which the designation "right-leg drive" can be attributed. However, in principle this third potential can also be detected at a different point on the patient.

The differential voltage measuring system according to an embodiment of the invention also has the interference signal measuring facility according to an embodiment of the invention. The differential voltage measuring system according to an embodiment of the invention shares the advantages of the interference signal compensation facility according to an embodiment of the invention and the interference signal measuring facility according to an embodiment of the invention.

The method according to an embodiment of the invention for generating an interference-reduced biological measurement signal is used to detect a possibly interference-afflicted measurement signal. Moreover, an electrode reference interference signal is detected via a measuring amplifier circuit for each sensor electrode. The respective measuring amplifier circuit is connected to the additional sensor lead via an electrical resistor and is configured to detect a change in electric potential occurring on the sensor lead and to determine an electrode reference interference signal therefrom. A reference common-mode-interference signal is also detected. A first interference-reduced measurement signal is determined based on the measurement signal and the reference common-mode interference signal.

Furthermore, an adapted reference electrode interference signal reduced by common-mode interference is determined based on the electrode reference interference signal determined by the interference signal measuring facility and the reference common-mode interference signal. Finally, a second interference-reduced measurement signal is determined based on the first interference-reduced measurement signal and the adapted reference electrode interference signal. The method according to an embodiment of the invention for generating an interference-reduced biological measurement signal shares the advantages of the interference signal compensation facility according to an embodiment of the invention and the interference signal measuring facility according to an embodiment of the invention.

A large proportion of the aforementioned components of the interference signal compensation facility according to an embodiment of the invention, in particular the evaluation unit, can be wholly or partially implemented in the form of software modules in a processor of a corresponding voltage measuring system. An extensively software-based implementation has the advantage that it is also possible to retrofit voltage measuring systems used to date in a simple way via a software update and adding the necessary hardware components, such as, for example, additional sensor leads and measuring amplifier circuits in order to work in the manner according to an embodiment of the invention.

In this regard, an embodiment is also directed to a corresponding computer program product with a computer program which can be loaded directly into a storage facility of a voltage measuring system with program sections for carrying out all the steps of the method according to an embodiment of the invention when the program is executed in the voltage measuring system. In addition to the computer program, a computer program product of this kind can optionally comprise additional parts such as, for example, documentation and/or additional components and also hardware components, such as, for example, hardware keys (dongles etc.) for using the software.

Transportation to the voltage measuring system and/or storage on or in the voltage measuring system can take place via a computer-readable medium, for example a memory stick, a hard disk or another kind of transportable or fixedly integrated data carrier on which the program sections of the computer program which can be read-in and executed by a computing unit of the voltage measuring system are stored. For this, the computing unit can, for example, have one or more interacting microprocessors or the like.

Further, particularly advantageous embodiments and developments of the invention may be derived from the claims and the following description, wherein the claims of one claim category can also be developed analogously to the claims and descriptive passages to create another category of claims and in particular also individual features of different example embodiments or variants can be combined to create new example embodiments or variants.

In one variant of the interference signal measuring facility according to an embodiment of the invention, the measuring amplifier circuit has a programmable amplifier circuit. Such a circuit enables the sensitivity of a measurement with an AD converter that is only able to process signals discretely and as a function of their operating voltage to be improved. Depending upon the type and manufacturer, the feedback can be changed by connecting individual pins (parallel), the SPI or I2C bus (serial) and thus the amplification can be adjusted. Sometimes, a programmable analog multiplexer which can be used to switch between the different input channels is also installed.

The measuring amplifier circuit is preferably electrically connected to the shield of a supply lead of the sensor electrode. The useful signal paths have at least one shield. The shield serves to keep electrical and/or magnetic fields occurring in particular at higher frequencies remote from the useful signal paths. Herein, it operates in accordance with the principle of induction or as a Faraday cage and is, for example, embodied as a metallic foil or the like surrounding the conductor of the useful signal path but insulated therefrom. Herein, every useful signal path can have a separate shield in the sense that every shield is attached to its own reference potential or its own evaluation electronics. However, the useful signal paths preferably have a common shield in the sense that shield parts surrounding the individual useful signal paths are connected in an electrically conductive manner and attached to a common reference potential or common electronics.

Herein, the shield can in principle be embodied as passive in that it is connected to the ground potential of the signal measuring circuit. However, it can preferably also be actuated actively via a corresponding driver in order to compensate the influence of any interference fields.

In principle, it is possible to measure the same interference signals on the shield as those that are also applied to the useful signal paths. This is because ambient electromagnetic fields, which are generally dominated by the common-mode components of the mains frequency, are coupled into the shield similarly to the coupling into the useful signal path. Therefore, in particular these components should be advantageously measured for the further analysis of the actual interference signals and the influence thereof on the bioelectric signals that are actually to be measured at the shield.

Therefore, contacting the shield enables the electrode reference interference signal to be obtained to be used according to the invention for interference suppression of the measurement signal.

In one variant of the differential voltage measuring system according to an embodiment of the invention, the measuring facility has a detection apparatus for detecting interferences on signal paths in the differential voltage measuring system.

The detection apparatus serves to detect interferences on signal paths in the differential voltage measuring system that have a shield. Herein, the detection apparatus comprises at least one analysis unit. The latter is connected to the shield and embodied to detect interference in a useful signal path of the voltage measuring system via a signal measured at the shield in the event of interference.

The analysis unit is embodied to detect interference in a useful signal path of the voltage measuring system. Therefore, according to an embodiment of the invention, interference is detected in that a—in optimal cases unexpected—signal, i.e. for example a bioelectric signal and/or a CM signal on the shield is measured and optionally analyzed in greater detail. Herein, the analysis unit can have a different embodiment. The detection apparatus can comprise exactly one analysis unit, but in other embodiments also a plurality of analysis units, such as, for example, a defect analysis unit and an interference signal evaluation unit. The analysis unit can preferably have an integrated circuit, particularly preferably an ASIC. However, the analysis unit can also preferably comprise a microcontroller or another type of universal computing unit.

Therefore, instead of only checking the useful signal paths or the actual cables to be checked, measurements and checks are performed on the shield as to whether the useful signal paths are defective or other types of interference have cross-coupled onto the shield. In contrast to applications known from practice, the useful signal paths do not have to be connected to the patient. Therefore, it is possible to test at any time point, i.e. for example, ahead of an examination but also during the examination, whether all the cables are in proper service condition and/or whether strong electromagnetic fields are coupled into the cables.

A further advantage of using a detection apparatus consists in the fact that technicians or service engineers are no longer required in order to detect a cable defect. The measurement on the shield can proceed in parallel and automatically during a useful signal measurement and a cable defect can be visualized immediately, for example on a user interface of the voltage measuring system. Therefore, the signal path defect, or cable defect, can be identified immediately, for example by the actual operator and the cable can be replaced immediately and a correct measurement performed. Therefore, this also reduces the risk of measurements continuing to be taken with cables with undetected damaged leads.

Moreover, the type of useful signal is of no importance when detecting interference via the shield. Therefore, the detection apparatus can be used for a wide variety of voltage measuring systems, such as, for example, EKG measuring systems, EEG measuring systems or EMG measuring systems without having to be specifically adapted for the purpose. This can also enable enormous savings on development and manufacturing costs.

Furthermore, the detection apparatus does not require an external voltage source for detecting interference since all relevant current-carrying parts can be integrated, or are integrated, in the detection apparatus or the voltage measuring facility. This enables a completely passive test structure.

The detection apparatus for detecting interference on signal paths in a differential voltage measuring system with a signal measuring circuit for measuring bioelectric signals with a number of useful signal paths preferably has an interference signal evaluation unit. This in turn comprises an interference signal-determining unit embodied to determine an interference signal with a frequency in the range of a mains frequency. The interference signal evaluation unit furthermore comprises an interference signal suppressing unit embodied to reduce interference signal components in the bioelectric signals based on the interference signal determined.

The detection apparatus described here can also be used as a stand-alone concept independently of the above-described detection apparatus, i.e. also without using the shield for detecting interference, when the interference signals are detected in another way, for example on a separate interference signal path. However, special synergetic effects are obtained when the determination according to the invention of the interference signal in the range of the mains frequency takes place by measurement at the shield. This is because the shield represents an electrical conductor with the same length as the useful signal paths. Ambient electromagnetic fields, which are generally dominated by the common-mode component of the mains frequency, are therefore coupled into the shield in a similar way to the coupling into the useful signal path. Therefore, in particular these components should be advantageously measured for the further analysis of the actual interference signals and the influence thereof on the bioelectric signals that are actually to be measured at the shield.

The mode of operation of a differential voltage measuring system was explained in detail above. The mains frequency designates the frequency of the mains voltage usually provided throughout the country by power supply companies or at least the frequency of the voltage of the electrical circuit to which the detection apparatus is attached. It has been found that the determination of interference signals can be greatly simplified if the frequency range of the interference signals is limited.

Therefore, according to an embodiment of the invention, the interference signal-determining unit only determines interference signals, in particular CM signals, within the range of the mains frequency. Since these usually represent the largest interference signal components, this results in a significant simplification of the signal analysis. During the signal analysis, the strongest signal in the frequency range around the mains frequency is sought, for example by way of a frequency analysis. This then has a high probability of representing mains interference since, as a rule, no useful signal components are found on the interference signal paths.

The signal found is then subsequently used for interference signal suppression, as will be explained in greater detail later. However, herein the signal is not, as was formerly usual, deformed in a wide range, which would reduce the diagnostic value, but only changed precisely within the usual tolerances of the previously determined frequency of the interference signal such that the influences of the interference signal are reduced or compensated.

The type of useful signal is of no importance when detecting interference via the shield and/or based on a range around the mains frequency. Therefore, the detection apparatus according to an embodiment of the invention can be used for a wide variety of voltage measuring systems, such as, for example, EKG measuring systems, EEG measuring systems or EMG measuring systems without having to be specifically adapted for this purpose. This also enables enormous savings on development and manufacturing costs.

Furthermore, the detection apparatus does not require an external voltage source for the detection of interference since all relevant current-carrying parts can be integrated, or are integrated, in the detection apparatus or the voltage measuring facility. This enables a completely passive test structure.

Herein, the detection apparatus can in each case be a stand-alone component and, for example, be installed connected upstream or interconnected as a retrofit kit in existing EKGs, EEGs or EMGs, for example via plug-in connections, as will be explained in greater detail later. However, the detection apparatus is preferably already permanently integrated in a voltage measuring system according to an embodiment of the invention.

The detection apparatus preferably comprises at least one current application unit embodied to impress a signal on a first useful signal path. The detection apparatus furthermore preferably comprises a defect analysis unit as an analysis unit which detects a signal path defect in a useful signal path of the voltage measuring system by way of the previously impressed signal measured at the shield in the event of interference.

Herein, the current application unit is preferably embodied such that it preferably impresses an arbitrary but defined first signal on a first useful signal path of the signal measuring circuit of the voltage measuring system. The signal can preferably be a current which can be directly or indirectly impressed and measured. For example, the current can preferably be impressed on a useful signal path via a current source. However, the current can also particularly preferably be impressed or regulated indirectly on the useful signal path via a pull-up resistor and/or a pull-up-down resistor. Herein, the impressed current is preferably in the nanoampere range in order, for example, not to falsify measured bioelectric signals and in this way to exclude the possibility of a patient being endangered.

If the useful signal path is, for example, connected to a patient via an electrode and the current application unit impresses a signal or a current on the first useful signal path, this current is discharged again via the patient and an appropriately configured return path connected to a patient.

An appropriately configured return path for the current impressed on the useful signal path is preferably a low-impedance return path to a common reference potential. Such a return path is, for example, formed by the first interference signal path. Since, due to their high input impedances, the useful signal paths do not form a low-impedance return flow path to the common reference potential (with intact leads), the impressed signal can only be discharged via the interference signal path. The consequence of this is that it is not only the above-described interference signals that are present on the interference signal path, but also the signal impressed on the useful signal path.

If a signal measuring cable or cable of a useful signal path is defective, in addition to the interference signal path, the signal measuring circuit has at least one further low-impedance return path for the impressed current. The impressed signal then passes into the shield and is no longer discharged via the interference signal path since the shield has the lower electrical resistance. Therefore, in the case of a cable defect, the signal on the interference signal path is no longer increased by the signal impressed on the useful signal path, instead, in this case, the impressed signal should be measured at the shield.

This measurement can be performed independently of whether or not the respective cable is connected to the patient. In this way, the cable defect can be identified before or also during an examination and corresponding countermeasures taken, such as, for example, a cable replacement.

In the case of a voltage measuring system as mentioned in the introduction, depending on its application, the signal measuring circuit can have any number of useful signal paths or signal measuring cables. As a rule, a signal measuring circuit, for example an EKG measuring system, has at least two useful signal paths. The useful signal paths preferably comprise electrodes which can be applied to a patient to be examined in order to measure an electric potential applied there. The electrode structure can depend upon the exact type of measurement, for example, whether it is an EKG measurement, an EEG measurement or an EMG measurement, and on where exactly the potential is to be measured on the patient. Suitable electrodes for different application purposes are known to the person skilled in the art.

The output from the electrodes is preferably connected to an amplifier circuit, preferably via the signal measuring cable. Particularly preferably, the electrodes are electrically connected to a differential amplifier. This amplifier forms a difference from the signals measured at its inputs and the signals detected by the electrodes and amplifies this difference. Moreover, the signal measuring circuit has a signal detecting unit which is connected to the output of the amplifier circuit in order to detect the amplified signals or, for example, the potentials and use them further and/or record them. For example, the signal detecting unit can have an A/D converter and further components in order to further process the digital signal.

The current application unit preferably in each case impresses different, i.e. unique, signals on different useful signal paths. This is particularly advantageous if the useful signal paths do not all have separate shields, but have a common shield, as will be explained in greater detail in the following.

As a rule, the shield or other interference signal paths do not have any direct current components or only have very few direct current components. If the signal is impressed on the useful signal path as direct current, it is very easy to distinguish the component from alternating current components which are more frequently coupled-in or otherwise present.

However, otherwise, it can also be advantageous to impress the signal as an alternating current on the useful signal path.

Therefore, the current application unit or current application control unit is preferably embodied such that it is able to impress an alternating current and/or a direct current on the useful signal paths.

Preferably, the current application unit is embodied such that the signals impressed on the useful signal paths have positive currents. Herein, in each case a positive current is impressed on the useful signal paths of the signal measuring circuit.

Thus, a number of N useful signal paths results in a total $I_g$ or total current $I_g$ of:

$$I_g = I_1 + I_2 + \ldots + I_N$$

Therefore, if there is no signal path defect, additionally to any interference signals applied, the total current impressed by the current application units is also discharged via the first interference signal path.

If the signal measuring circuit has a plurality of useful signal paths, a saturation effect may occur if all useful signal paths are exposed to a positive current.

In order to impress different currents or signals on the useful signal paths, the detection apparatus quite particularly preferably has one current application unit per useful signal path. A current application unit preferably comprises a current source. However, particularly preferably and, as already mentioned, the current application unit comprises a pull-up or pull-down resistor which regulates the voltages up or down along the useful signal paths and hence indirectly influences the impressed currents on the respective useful signal path.

Herein, the current application unit is preferably embodied such that it impresses a positive current on a number of useful signal paths and a negative current on a number of useful signal paths. Particularly preferably, the number of useful signal paths on which a positive current is impressed corresponds to the number of useful signal paths on which a negative current is impressed. As a result, a useful signal path can be exposed to a positive current and a useful signal path to a negative current in alternation. In the case of one or more cable defects, this results in a total current of:

$$I_D = \sum_i I_{Pi} + \sum_j I_{Nj}$$

$I_D$: defective current
$I_{Pi}$: positive current in the useful signal path i
$I_{Nj}$: negative current in the defective useful signal path j Particularly preferably, the sum totals of all defective currents, i.e. all possible combinations of the impressed currents are also unique or individual. If a current can now be measured on the shield, the useful signal path or paths with a signal path defect can be identified quickly and easily from the value of the signal component or signal components.

It is precisely with complex cable trees with up to 200 leads, as is the case, for example, with intracardiac EKGs, such as, for example, in angiography applications, that this enables targeted detection of the defective lead. Thus, instead of replacing a complete highly complex cable costing up to €1000, it is possible to replace a single lead costing €10-20.

In order to check whether the impressed signals on the individual useful signal paths are within the measuring range, the fault detection unit preferably does not comprise one overall comparison unit for all useful signal paths, but has one comparison unit for each useful signal path. Preferably, the comparison units each have an AD converter, however, particularly preferably they also each comprise a comparator.

Due to possible further tolerances and parasitic currents in the voltage measuring system, the impressed signals preferably differ for each useful signal path by at least 5 nA and/or at most 20 nA. Quite particularly preferably by about 10 nA.

In the case of a signal path defect, in order easily to find the useful signal path with the defect, alternatively or additionally, the current application unit is preferably embodied such that it is able to switch the impressed signals individually for each useful signal path. For example, following the detection of a signal path defect, for example, the impression of a signal on a useful signal path can be deactivated gradually in each case. If the deactivation of a signal on a useful signal path does not cause a change to the total signal on the interference signal path, this useful signal path has a cable defect.

Preferably, the detection apparatus furthermore comprises at least one first interference signal path for measuring a first interference signal. As described above, common-mode interference signals frequently occur during the measurement of bioelectric signals, for example.

The first interference signal path is preferably connected to the patient via an electrode. Therefore, the third useful signal path can preferably coincide wholly or at least partially with the first interference signal path, as will be described in greater detail below, or correspond thereto at least in sections. For example, the same electrode and the same cable can be used for the third useful signal path and the first interference signal path. Therefore, it is not then necessary for the operator to attach additional electrodes to the patient in order to check the signal path according to the invention or to carry out other special measures.

The first and/or the third interference signal path preferably has a current measuring unit. This current measuring unit preferably comprises a current measuring resistor, preferably a shunt resistor, and a voltage measuring facility connected in parallel thereto.

Herein, the current measuring resistor can be connected between the third electrode and the driver circuit of the signal measuring circuit, i.e. the right-leg drive.

It is preferable for the shunt resistor to have at least one resistance value of 10 kΩ and a maximum resistance value of 1000 kΩ.

The voltage measuring facility is preferably also a differential amplifier. At the output of the voltage measuring facility, the interference signal path has an interference signal detecting unit to enable the measured interference signal to be further processed. The interference signal detecting unit comprises, for example, an A/D converter and a unit for further processing the digital signal.

For example, it is possible to search within the first interference signal or a signal resulting or further processed therefrom, for example in the time and/or frequency domain, for typical features of the bioelectric signal, for example in an EKG signal, for the typical EKG waves.

Preferably, a detection apparatus according to an embodiment of the invention comprises at least one first comparison unit which checks whether the signal of a useful signal path is within a measuring range.

For this purpose, preferably a defined measuring range or a threshold value can be selected above which it is assumed that the signal flows on the useful signal path.

As a rule, i.e. with intact useful signal paths or cables, the input impedances of the measuring leads of the cables of an EKG measuring system are high.

If the electrodes are attached to the patient, preferably a check is performed via at least the first comparison unit as to whether the signal which was impressed on the first useful signal path is within a measuring range. At the same time or even after this, at least one first interference signal is measured on at least the first interference signal path.

If, contrary to expectations, the useful signal path is not connected to the patient, for example because the electrode has become detached from the patient, the current circuit is closed or the impedance to be overcome by the impressed signal is significantly higher.

Therefore, the voltage produced by the current application unit, for example at the electrode of the first useful signal path, goes into saturation. Herein, the current can, for example, be detected indirectly via a resistance as a voltage. Hence, the impressed signal is therefore outside of the defined measuring range.

This check or measurement is performed via the comparison unit. Therefore, the comparison unit can check whether or not the useful signal path is connected to a patient. However, on its own this does not provide any information on whether there is a signal path defect of a useful signal path connected to a patient.

Therefore, the impressed current is discharged via the first interference signal path in the case of intact and attached leads but via the shield in the case of a cable defect. Therefore, if, as described above, it has been established that the cables are correctly attached to the patient, a cable defect can be established not only from the current additionally flowing on the shield. The cable defect can moreover also be established from the absence of any current or signal on the first interference signal path. Hence, two methods for the identification of cable defects can be provided and optionally combined without any significant extra effort.

The detection apparatus preferably has a second interference signal path for measuring a second interference signal.

This interference signal path can be constructed in a different way. It can be constructed such that no bioelectric signals are coupled in. However, preferably interference signals can be coupled-in that also occur on the first interference signal path, such as, for example, the above-described common-mode interference signals. The second interference signal path can preferably serve for the reference measurement for the interference signal on the first interference signal path.

Herein, the second interference signal path does not have to comprise a signal measuring cable but can correspond to a capacitive measurement or coupling to ground.

The second interference signal path preferably extends between a reference potential of the voltage measuring system or of the EKG measuring system and an external reference potential, for example the ground potential. This electric coupling preferably extends via a capacitive coupling. Since the second interference signal path is only coupled to the voltage measuring system via the common reference potential, the second interference signal on the second interference signal path is largely independent of the input impedances of the cables used in the useful signal paths. Therefore, the second interference signal path cannot serve as a return path for the signals impressed on useful signal paths. Moreover, due to the structure of the second interference signal path, the interference signal is therefore largely determined from common-mode interference signals.

To implement the capacitive coupling, the second interference signal path preferably has a conductor surface electrically connected to the reference potential of the voltage measuring system between the voltage measuring system and the ground potential. Herein, the conductor surface corresponds to a coupling capacitance. The conductor surface can, for example, be implemented by a metal plate or foil.

The second interference signal path can also have a current measuring unit. Herein, the current measuring unit can preferably be connected between the reference potential of the voltage measuring system and the capacitive link to the external reference potential of the conductor surface. In addition, this current measuring unit can also preferably have a current measuring resistor and a voltage measuring facility connected in parallel thereto. The current measuring resistor is preferably a shunt resistor and the voltage measuring facility is preferably a differential amplifier.

The second interference signal path can have an interference signal detecting unit, for example at the output of the voltage measuring facility.

The detection apparatus preferably has an interference signal evaluation unit as an analysis unit which measures a third interference signal at the shield. Hence, the shield serves as a third interference signal path. As described above, this is particularly advantageous since the shield represents an electrical conductor with the same length as the useful signal paths. Therefore, ambient electromagnetic fields, which are generally dominated by the common-mode component of the mains frequency, are coupled into the shield similarly to the coupling into the useful signal path. This enables a particularly expedient and simplified analysis of the interference signals in particular in relation to the bioelectric signals that are actually to be measured.

If at least two interference signal paths are used, the interference signal evaluation unit can preferably be connected to all the interference signal paths. The interference signal evaluation unit is then preferably embodied to form a combination signal of the first interference signal, the second interference signal and/or the third interference signal.

For example, a signal path defect or cable defect can in particular be verified if the signals impressed on the useful signal paths can be detected in the difference signal with the shield or the third interference signal path. Therefore, the difference signal is, for example, composed of the first and/or second interference signal and the third interference signal by way of weighted addition or subtraction. Herein, the weighting can be adapted in a suitable manner.

If a current is impressed on a useful signal path as an alternating current, it may be the case that this current is very similar to the current on the first interference signal path. If a difference signal is now formed from the first and second interference signal, it is easier to detect the currents cross-coupled by the useful signal path.

However, the combination signal can, for example, also comprise a ratio of the first and second interference signal.

The interference signal evaluation unit preferably comprises an interference signal suppressing unit embodied to reduce interference signal components of the useful signals based on at least one of the interference signals determined. This can, for example, take place in that the measured useful signals are reworked as will be described in greater detail later. However, alternatively or additionally, active counter-regulation can also be performed on the patient via a corresponding driver (RLD) during the detection of the measurement signals.

The range of the mains frequency for the determination of the interference signal is preferably ±2%, particularly preferably ±1%, of a desired mains frequency. This substantially defines the frame that should not be left in the case of a functioning power network. Therefore, it is advantageous, to restrict the analysis to this range.

Herein, the actual mains frequency can deviate from the desired value for the desired mains frequency. The desired mains frequency is, for example, 60 Hz in North America, Central America and parts of South America and in Japan, Taiwan, the Philippines etc. or, for example, 50 Hz in the other parts of the world.

The interference signal suppression preferably takes place in that, for example, the information on this signal is used to set a frequency-based filter which can advantageously have a narrower bandwidth than was formerly usual in the prior art. The influence of the interference signals and the filtering process on the useful signals or the bioelectric signals can advantageously be reduced.

Alternatively, to suppress interference signals, it is preferably also possible to use a phase-locked loop (PLL) that receives the interference signal determined according to the invention as a generator input signal. A PLL is an electronic circuit arrangement that influences the phase angle and hence also the frequency of a variable oscillator via a closed control loop such that the phase difference between an external reference signal (the interference signal) and a signal derived therefrom is as constant as possible. Hence, the PLL is advantageously provided with very precise information on the frequency of the interference signal so that it now only has to determine the possibly displaced phase or different amplitude of the interference in the useful signals or the bioelectric signals. As a result, the PLL advantageously converges more quickly to the final quality of the interference-suppressed signal.

The detection apparatus preferably has an output unit attached to the output of the interference signal evaluation unit and/or operates externally, for example via radio transmission. The output unit serves to output a detected signal path defect or signal it immediately. Herein, this outputting or signaling can take place in situ, for example visually or acoustically. Moreover, the signaling can be sent by radio, for example to a service engineer. A further output form can take place as logging, for example together with the measurement data. Particularly preferably, the logging is temporally correlated with the measurement signal or the bioelectric signals to be measured. Thus, it is, for example, possible in the case of interference that only occurs intermittently, as in the case of a loose contact, to document which measured values are usable and which are not usable.

In particular if the detection apparatus is integrated in the voltage measuring system, the output unit is preferably included in a user interface of the voltage measuring system. This, for example, enables the operator simultaneously to check the bioelectric signals on the user interface, for example, a monitor, and detect a cable defect.

In the figures, in each case an EKG measuring system 1 is assumed by way of example to be a differential voltage measuring system 1 for measuring bioelectric signals S(k), here EKG signals S(k). However, embodiments of the invention is not limited thereto.

FIG. 1 shows by way of example an arrangement 10 with an EKG measuring system 1 according to the invention on a patient P. The EKG measuring system 1 comprises an EKG device 27 with its electrical connectors and electrodes 3, 4, 5 attached thereto by cables (e.g., supply leads) K in order to measure EKG signals S(k) on the patient P. With the aid of the invention, this EKG measuring system 1 is able to suppress interference signals coupled into the electrodes 3, 4, 5 (as can be seen, for example, in FIG. 5).

The measurement of the EKG signals S (k) requires at least one first electrode 3 and one second electrode 4 that are attached to the patient P. Signal measuring cables K connect the electrodes 3, 4 via connectors 25a, 25b, generally plug-in connections 25a, 25b, to the EKG device 27. Herein, together with the signal measuring cables K, the first electrode 3 and the second electrode 4 form a part of a signal detecting unit 9 (see FIG. 2) with which the EKG signals S(k) can be detected.

A third electrode 5 serves as a reference electrode in order to establish potential equalization between the patient P and the EKG device 27. This will be explained in greater detail later. This third electrode 5 is conventionally attached to the patient's right leg (for which reason, as mentioned above, this connector is often also called a "right-leg drive" or "RLD"). However, as in this case, it can also be positioned at a different location. Furthermore, further connectors, not depicted in the figures, on the EKG device 27 can attach a plurality of further contacts for further leads (potential measurements) to the patient P that are used to form suitable signals.

The voltage potentials UEKG34, UEKG45 and UEKG35 that serve to measure the EKG signals S(k) form between the individual electrodes 3, 4, 5.

The directly measured EKG signals S(k) and/or further processed bioelectric signals Sest(k) are displayed on a user interface 14 of the EKG device 27.

During the EKG measurement, the patient P is at least capacitively coupled into the ground potential E (depicted schematically in FIG. 1 by a coupling on the head and the right leg). However, the patient is exposed to a source of interference Ucm, for example an electrical field produced by the power supply with a 50 Hz alternating current, and the resulting interference signal nsource(t) present via the patient P and which changes constantly with time t and which is inevitably also detected by the relatively sensitive measurement. As a rule, this source of interference Ucm causes interference signals via the patient P to be coupled into the measuring leads in the signal measuring cables K; this will be referred to later.

Herein, the signal measuring cables K leading from the first electrode 3 and the second electrode 4 to the EKG device 27 are part of the useful signal paths 6a, 6b. Herein, the signal measuring cable K leading from the electrode 5 to the EKG device 27 corresponds to part of a third useful signal path 7N. The third useful signal path 7N transmits interference signals from the source of interference Ucm which were coupled-in via the patient P and the electrodes.

The cables K have a shield S, here depicted schematically by dashed lines as a cylinder surrounding all the useful signal paths 6a, 6b, 7N. However, the shield does not have to surround all the cables K jointly, instead the cables K can also be shielded separately. However, the connectors 25a, 25b, 25c preferably in each case have an integrated pole for the shield. These poles are then brought together on a common shield connector 25d. Herein, the shield S is, for example, embodied as a metal foil surrounding the conductor of the respective cable K, but insulated from the conductor.

To detect interference signals coupled into the first and/or second useful signal path, the EKG device has an interference field measuring circuit 60, which measures a change in potential on the shield S occurring on account of electric fields coupled into the electrodes.

To identify cable defects D, the EKG measuring system 1 can optionally have a detection apparatus 40 which will be explained in greater detail with reference to FIG. 5. The cables K are checked for cable defects D with this aid of this detection apparatus 40. The check signal PS generated by the detection apparatus 40 which signals a cable defect D can, as shown in FIG. 1, be displayed and depicted by an output unit 16' on the user interface 14 of the EKG device 27. This enables not only the EKG signals, but simultaneously also the cables K to be monitored on the user interface 14 S(k) for any possible cable defect D.

However, the output unit 16 does not mandatorily have to be integrated in the user interface 14. The signaling can, for example, also be implemented via a signal lamp, for example in the form of an LED (light-emitting diode) or the like, that signals a defect. However, additionally or alternatively, it can also take place acoustically, for example via a warning bleep. A further variant is also an external transfer, for example via radio, to a service engineer or to be output in a measuring log in order in this way to display or log a cable defect D. Moreover, as shown in FIG. 1, the EKG device 27 can have an external interface 15 in order, for example, to provide a connector for a printer, a storage facility and/or even a network.

Figure 2:
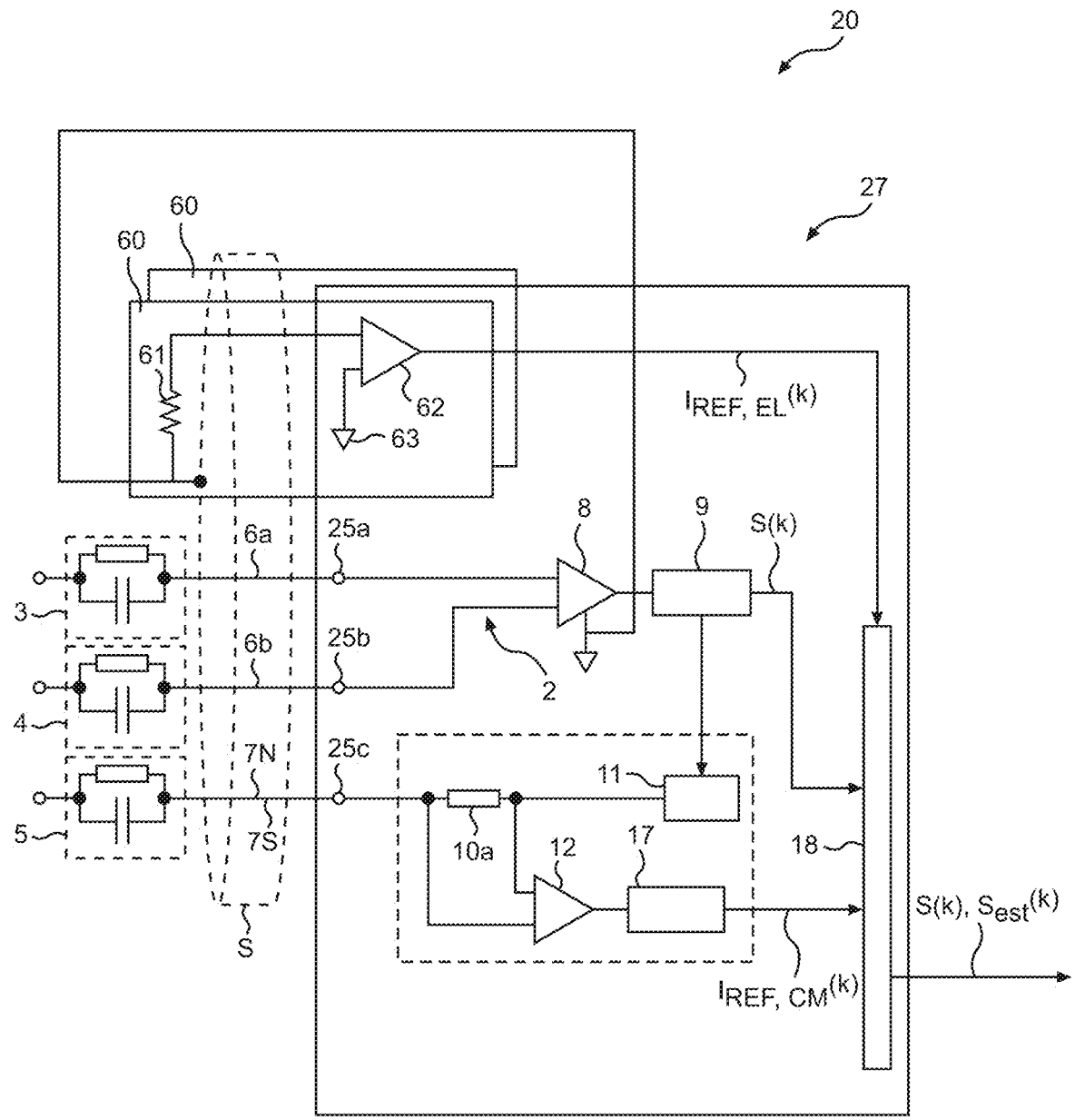

FIG. 2 is a very rough illustration of a schematic example embodiment of an EKG measuring system 20 according to an example embodiment of the invention in greater detail in a block diagram.

The EKG measuring system 20 comprises a signal measuring circuit 2 that serves to measure the bioelectric signals S(k).

Here, as already mentioned above, the signal measuring circuit 2 has three useful signal paths 6a, 6b, 7N. As described in respect of FIG. 1, the useful signal paths are electrically connected via the electrodes 3, 4, 5, the cables K and the plug-in connection 25a, 25b, 25c from the patient P to the EKG device 27. Here, the electrodes 3, 4, 5 are depicted in a simplified manner as an RC element and illustrate the impedance values of the useful signal paths 6a, 6b, 7N.

The first electrode 3 and the second electrode 4 are in contact with the patient P. Due to a difference in potential between the lead points at which the electrodes 3, 4 are fastened to the patient, a useful signal, for example a "cardiac current" is transmitted from the electrodes 3, 4 to an amplifier circuit 8, for example an operational amplifier. The amplifier circuit 8 comprises two inputs by which it is electrically connected to the first electrode 3 and second electrode 4. The output signal from the amplifier circuit 8 is transferred to a signal detecting unit 9 which detects the useful signal amplified by the amplifier circuit 8. Herein, the first useful signal path 6a extends from the contact of the first electrode 3 to the patient P via the first electrode 3 to the input of the amplifier circuit 8. The second useful signal path 6b extends from the contact of the second electrode 4 to the patient P via the second electrode 4 to the input of the amplifier circuit 8.

The third electrode 5 described in respect of FIG. 1 is part of the first interference signal path 7S. It is electrically connected via the cable K to a current measuring resistor 10a, hereinafter called a shunt resistor. The shunt resistor 10a is moreover electrically connected to a driver circuit 11 which, as already explained, is also called a right-leg drive. The driver circuit 11 is constructed such that a reference potential corresponding to the common-mode voltages with EKG components is applied to the patient via the electrode 5. For example, this reference potential can be set in a known manner to an inverse, amplified mean value of the measuring leads. This enables the reference potential to be established at the common-mode voltage.

The reference signal $I_{REF,CM}$ generated in the RLD circuit is also transferred to an evaluation unit 18 which also receives the measurement signal S(k) detected with the aid of the first and second electrode 3, 4 and outputs an interference-suppressed signal $S_{est}(k)$.

Another part of the measuring circuit 20 shown in FIG. 2 is an interference field measuring circuit 60 embodied for every electrode 3, 4 which measures a change in potential on the shield S occurring on account of the electric fields coupled into the electrodes. For the measurement, the interference field measuring circuit 60 in each case has an additional lead 65, a shunt resistor 61 and a measuring amplifier 62. The electrode reference interference signal IRef,El(k) generated by the measuring circuit 60 is also transferred to the evaluation unit 18.

Figure 3:
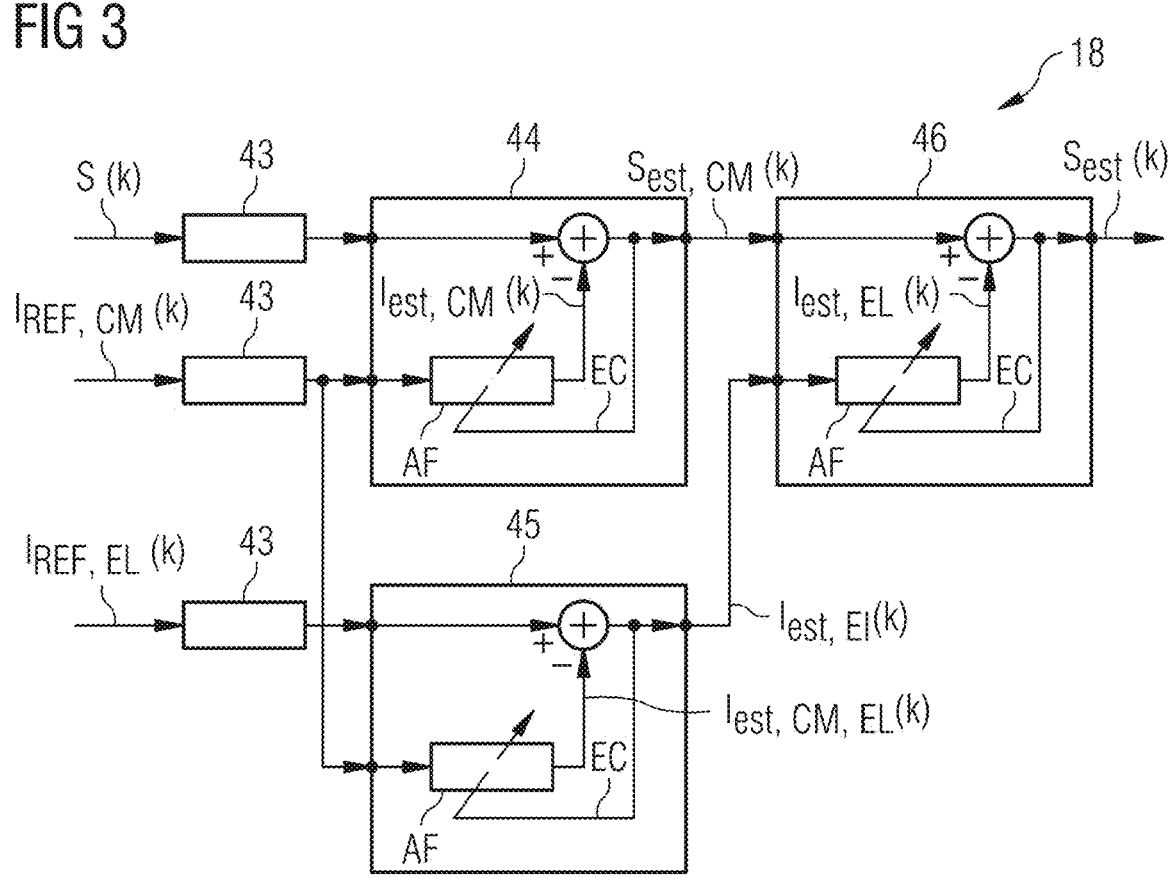

FIG. 3 is a schematic depiction illustrating an evaluation unit 18 according to an example embodiment of the invention. The evaluation unit 18 in each case has inputs or digital filters 43 which detect and filter the signals S(k), $I_{REF,CM}$, $I_{Ref,E1}(k)$ generated by the signal measuring circuit 2, the driver circuit 11 and the measuring circuit 21. The filters 43 are usually embodied as bandpass filters or blocking filters.

Herein the measurement signal S(k) carries signal interference components $I_{EKG,CM}(k)$ generated by the coupling of electric fields into the body and signal interference components $I_{EKG,EL}(k)$ generated by the coupling of electric fields into the electrodes 3, 4.

$$S(k)=I_{EKG}(k)+I_{EKG,CM}(k)+I_{EKG,EL}(k).$$

Together with the reference signal $I_{REF,CM}$ for the interferences on the body, a first adaptive filter 44 generates an interference-reduced signal $S_{est,CM}(k)$ containing fewer signal components that are coupled into the body. During the filtering process, a correction signal $I_{est,CM}(k)$ is estimated as the interference signal and combined with the incoming signal S(k) to form the interference-reduced signal $S_{est,CM}(k)$.

However, this interference-reduced signal $S_{est,CM}(k)$ also already contains fewer signal components of the interference coupled into the electrode. For this reason, the electrode reference interference signal $I_{Ref,E1}(k)$ can no longer be used as a reference for this already partially interference-suppressed signal $S_{est,CM}(k)$ for further filtering. For this reason, an adapted electrode interference signal $I_{est,E1}(k)$ is additionally generated with the aid of a second adaptive filter 45 based on the electrode reference interference signal $I_{Ref,E1}(k)$ and the reference interference signal $I_{REF,CM}(k)$ coupled into the body of the patient. During the filtering process, a correction signal $I_{est,CM,EL}(k)$ is estimated as the interference signal and combined with the incoming reference interference signal $I_{Ref,E1}(k)$ to form the adapted electrode interference signal $I_{est,E1}(k)$.

Finally, the adapted electrode interference signal $I_{est,CM}(k)$ is used for adaptive filtering in a third adaptive filter 46 of the already partially interference-reduced signal $S_{est,CM}(k)$ in order to obtain an almost interference-free end signal $S_{est}(k)$. During the third filtering process, a correction signal $I_{est,EL}(k)$ is estimated as the interference signal and combined with the incoming interference-reduced signal $S_{est,CM}(k)$ to form the almost interference-free end signal $S_{est}(k)$.

Figure 4:
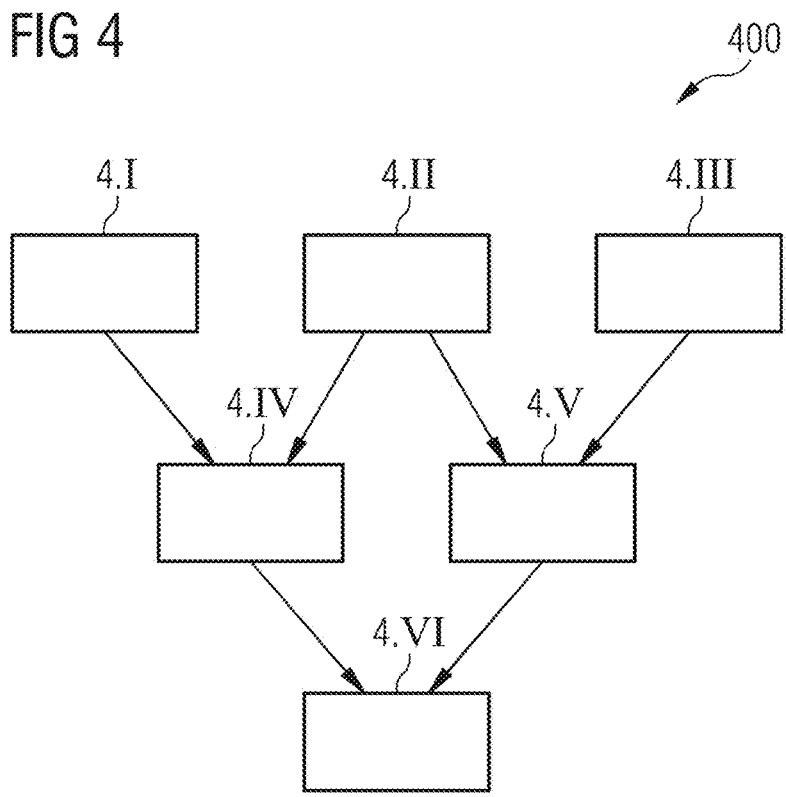

In FIG. 4 shows a flowchart 400 illustrating a method for generating an interference-reduced biological measurement signal according to an example embodiment of the invention. In step 4.I, initially, a measurement signal S(k) is first detected and bandpass-filtered. In parallel thereto, in step 4.II a signal interference component $I_{REF,CM}(k)$ generated by the coupling of electric field into the body is measured.

Further in parallel, in step 4.III signal interference components $I_{REF,EL}(k)$ generated by the coupling of electric fields into the electrodes 3, 4 are measured. In step 4.IV, there is a first adaptive filtering process in which the two signals S(k) and $I_{REF,CM}(k)$ detected in steps 4.I and 4.II are combined with one another by weighted subtraction. Herein, the weighting can be varied as required, i.e. for example according to the strength of the respective couplings-in or interference fields. This process generates a signal $S_{est,E1}(k)$ that is largely freed of signal interference components generated by the coupling of electric fields into the body. Furthermore, in step 4.V, the two reference interference signals $I_{REF,CM}(k)$, $I_{REF,EL}(k)$ generated in steps 4.II and 4.III are used as the basis for the generation of an adapted electrode reference interference signal $I_{est,E1}(k)$ which is already free of signal components which relate to interference coupled into an electrode 3, 4 of the useful signal path but which is already contained in the reference interference signal $I_{REF,CM}(k)$ generated in step 4.II. In this way, an adapted electrode reference interference signal $I_{est,E1}(k)$ is generated.

In step 4.VI, the adapted electrode reference interference signal $I_{est,E1}(k)$ is combined in a third adaptive filtering process with the signal $S_{est,CM}(k)$ generated in step 4.IV by weighted subtraction. Herein, the result is the generation of a largely interference-suppressed signal $S_{est}(k)$ containing neither significant interferences that have arisen from the coupling of electric fields into the body nor significant interferences that have arisen from the coupling of electric fields into the electrodes 3, 4.

Figure 5:
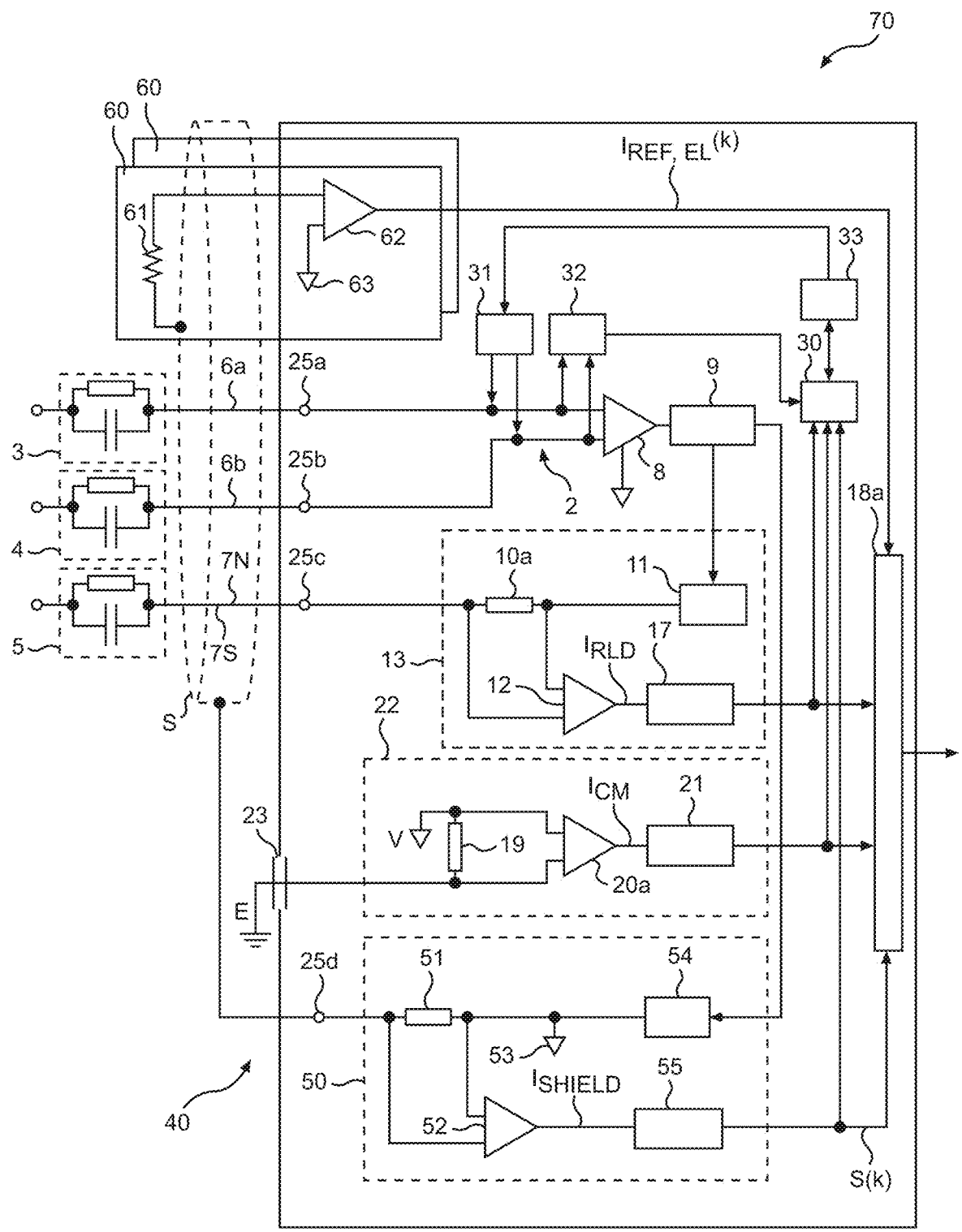

FIG. 5 illustrates a second example embodiment of an EKG device 70 of an EKG measuring system 1 in greater detail in a block diagram.

In addition to the components shown in FIG. 2, the EKG device 70 shown in FIG. 5 has a detection facility 40 with a current application unit 31. This can, on the one hand, impress a first signal, here a first current $I_{E1}$ in the nanoampere range, on the first useful signal path 6a. On the other hand, it can impress a second signal $I_{E2}$, here a second current $I_{E2}$ in the nanoampere range, on the second useful signal path 6b. Moreover, here, the second current $I_{E2}$ is a current that is 10 nA higher than the first current $I_{E1}$.

Currents are regulated via a current application control unit 33 which communicates with the current application unit 31 and a defect analysis unit 30 which will be described later.

In the case of intact signal measuring cables, apart from the interference signal path 7S, there is no further low-impedance return path to the common ground potential for the first current IE1 and the second current $I_{E2}$.

The means that it is not only the interference signals ICM that are present on the interference signal path 7S, but also the current IE1 impressed on the first interference signal path 6a and the current IE2 impressed on the second useful signal path 6b.

Therefore, with intact useful signal paths 6a, 6b, the following interference signal $I_{RLD}$ is obtained on the first interference signal path 7S:

$$I_{RLD}=I_{CM}+I_{E1}+I_{E2}.$$

Here, the current application unit 31 has only been depicted once by way of example, but it can, for example, be implemented via a first current source which impresses the first current IE1 on the first useful signal path 6a and a second current source which impresses the second current IE2 on the second useful signal path 6b.

The voltages that were generated by the current application unit 31 at the first electrode 3 and the second electrode 4a are regularly at the most in the millivolt-range. This is because the impressed currents are discharged in the nanoampere range through an impedance which can be in a range of about 50 kOhm to 2 MOhm. Hence, this impedance is in any case lower than that of the useful signal paths. However, if the first useful signal path 6a and/or the second useful signal path 6b is not electrically connected to the patient P, the current circuit is not closed or the impedance to be overcome by the impressed current is significantly higher. As a result, the voltage generated by the current sources at the electrode which is not in contact with the patient P goes into saturation. To check this, the detection apparatus 40 has a comparison unit 32.

Here, for clarity, the comparison unit 32 was only depicted as a block. However, here there is preferably in each case a comparison unit for the first useful signal path 6a and for the second useful signal path 6b. Here, the comparison units 32 comprise comparators. If the currents determined on the first useful signal path 6a and on the second useful signal path 6b are within a predefined measuring range, the first electrode 3 and the second electrode 4 are electrically connected to a patient and the comparators 32 report two connected electrodes.

If, for example, only one connected electrode is reported, a user of the EKG device 70 can check the electrodes immediately and re-attach them if necessary.

As described above, the electrodes are attached to the EKG device 70 via signal measuring cables K. To make the application of the EKG measuring system 1 on the patient P as simple as possible, the cables K should be narrow, light and at the same time shielded. However, this combination of features often results in cable defects D. These cable defects D can occur after bending or torsion of the cables K. This can result in irreversible bulging of the measuring leads which ruptures the insulation of the leads. The rupturing of the insulation of the leads can result in contact between the measuring leads and the shield S. This contact results in a reduction of the input impedance and the amplification of interferences.

The reduction of the input impedance of the cable K in the case of a cable defect D results in a further low-impedance return flow path for the respective impressed current via the shield S. If, for example, there is a cable defect D in the first useful signal path 6a, the current Im is discharged via the shield S and hence no longer increases the current $I_{RLD}$ on the interference signal path 7S. However, the comparator 32 does not identify this incorrectly discharged current and continues to indicate that the electrode 3 is electrically connected to the patient P.

In now to be able to detect this cable defect D, the detection apparatus 40 has three interference signal paths 7S, 22, 50.

The useful signal paths 6a, 6b comprise the first electrode 3 and the second electrode 4, the cables K, the current application unit 31, the comparison unit 32 and the further lead inside the device (with the amplifier circuit 8) as far as the signal detecting unit 9 also a dual function here. Namely, they belong on the one hand to the signal measuring circuit 2 in order to measure bioelectric signals S(k). On the other hand, they belong to the detection apparatus 40 in order to check whether, or optionally how many, electrodes of the corresponding useful signal paths 6a, 6b are connected to a patient or are defective.

The signal IRLD output by the interference signal evaluation unit 13 is analyzed in a defect analysis unit 30 together with the data from the comparison unit 32. If the comparison units 32 report that all electrodes are connected and the interference signal evaluation unit 13 outputs a current $I_{RLD}$ comprising the interference signals $I_{RLD}$ and the first impressed current Im and the second impressed current $I_{E2}$, the defect analysis unit 30 detects that all the electrodes are connected to the patient P and there is no cable defect D.

In the case of a defect, for example in the useful signal path 6a, the current $I_{E1}$ is discharged via the shield S. To measure this defective current, the third interference signal path 50 has a current measuring unit 51, 52.

For the third current measuring unit 51, 52, a third shunt resistor 51 is connected between the internal reference potential 53 which can be the same reference potential as V and the connector 25*d* of the shield S is used as a current measuring resistor. Moreover, a third voltage measuring facility 52 connected in parallel thereto is used. Herein, the third voltage measuring facility 52 can again be implemented by an amplifier, for example a PGA. The voltage measuring facility 52 is also connected to a third interference signal detecting unit 55 which is embodied, for example, as an A/D converter and digitizes, and optionally further processes, the measured signals $I_{SHIELD}$.

Moreover, a cable driver 54 is arranged on the third interference signal path 50 which is connected to the signal detecting unit 9. This enables a reference potential complementary to the common-mode voltages to be applied to the shield S. This enables an approximation of the ambient interference fields or the main voltage.

However, the detection apparatus 40 does not have to be integrated in the EKG measuring system, as shown, for example, in FIG. 5. It can also be installed in an existing EKG measuring system via plug-in connections, for example, or also be connected upstream or interconnected. Such retrofitting enables cable defects D also to be detected with an already existing EKG measuring system.

To display the EKG signals S(k) or $S_{est}$(k) and any possible cable defects D via a check signal PS (see FIG. 1) in parallel on the user interface 14, this is attached to the signal detecting unit 9 of the signal measuring circuit 2 and to the defect analysis unit 30 of the detection apparatus 40. This is roughly illustrated in a schematic manner in FIG. 1. Therefore, the user interface 14 is shown with a corresponding output unit 16' in FIG. 1.

The above-described further output unit 16 for, for example, visual and/or acoustic signaling of a cable defect D can also be coupled to an output of the interference signal evaluation unit 18*a* and the defect analysis unit 30.

Moreover, as already mentioned, the differential voltage measuring system 1 is equipped with an external interface 15 for example for a network, a printer and/or a storage device etc. which can, for example, be connected by signal technology to the signal detecting unit 9 of the signal measuring circuit 2 and/or defect analysis unit 30.

The detection apparatus 40 has three interference signal paths 7S, 22, 50. As with the example embodiment in FIG. 2, the first interference signal path 7S comprises the third electrode 5 which is attached by its input to a patient P and extends to the shunt resistor 10*a* which is electrically connected to the output of the electrode 5. Here, the voltage that drops across the shunt resistor 10*a* is also measured by the first voltage measuring facility 12 connected in parallel to the shunt resistor 10*a*. The interference signal IRLD measured thereby is then digitized, further processed and detected by a first interference signal detecting unit 17 connected to the output of the first voltage measuring facility 12.

The detection apparatus 40 furthermore comprises a second interference signal path 22 with a current measuring unit 19, 20*a*. This second current measuring unit 19, 20*a* measures the current flowing from an internal reference potential V of the EKG device 70 via a capacitive coupling to an external fixed reference potential E, the ground potential E. This second measured interference signal ICM is again primarily common-mode interference signals. The capacitive coupling between the EKG device 70 and the ground potential E is still present. In order to provide a defined interference signal path 22 for this interference signal ICM at which the interference signal ICM can be measured effectively, a larger conductor surface 23, for example in the form of a metal plate or a foil, is connected to the internal reference potential V of the EKG device 70 which forms a "capacitor surface" to the ground potential E. In this second interference signal path 22, the second current measuring unit 19, 20*a* is connected between the internal reference potential V and the conductor surface 23.

For the second current measuring unit 19, 20*a*, a current measuring resistor 19, hereinafter called the second shunt resistor, connected between the internal reference potential V and the conductor surface 23 and a second voltage measuring facility 20*a* connected parallel thereto is used for current measurement on the second interference signal path 22. Herein, the second voltage measuring facility 20*a* can again be implemented by an amplifier, for example a PGA.

The measured second interference signal ICM is detected by an interference signal detecting unit 21 connected to the output of the voltage measuring facility 20*a*, for example digitized and optionally further processed by an A/D converter.

The three interference signal detection units 17, 21, 55 of the respective interference signal paths 7S, 22, 50 are connected to a—here preferably digitally operating—interference signal evaluation unit 18 and to the defect analysis unit 30.

The interference signal evaluation unit 18*a* is configured to process the first interference signal $I_{RLD}$, the second interference signal $I_{CM}$ and the third interference signal $I_{SHIELD}$. As a result, the common-mode third interference signal path 50 can be separated or distinguished from the cross-coupled currents $I_{E1}$, $I_{E2}$ occurring there in the case of defective cables K or measuring leads K. This makes it easier to verify a cable defect D. To evaluate the interference signals $I_{RLD}$, $I_{CM}$, $I_{SHIELD}$ which are present in digital form here, the interference signal evaluation unit 18 can again be implemented by a computing facility with suitable software and/or, for example, also by one or more ASICs.

Preferably, the interference signal evaluation unit 18*a* can be embodied such that an output signal $I_{REF,CM}$(k) is generated from the interference signals $I_{RLD}$, $I_{CM}$, $I_{Shield}$) as will be explained in greater detail with reference to FIG. 6.

Another part of the measuring circuit 70 shown in FIG. 5 is an interference field measuring circuit 60 embodied for every electrode 3, 4 which measures a change in potential on the shield S occurring on account of the electric fields coupled into the electrodes. For the measurement, the interference field measuring circuit 60 in each case has a shunt resistor 61 and a measuring amplifier 62. The electrode reference interference signal $I_{Ref,E1}$(k) generated by the interference field measuring circuit 60 is also transferred to the evaluation unit 18*a*.

Therefore, in addition to improved interference signal compensation, a cable defect D in an EKG System 1 can be detected immediately and unequivocally with the aid of the measuring circuit 70 illustrated in detail in FIG. 5. This does not require a separate test procedure to be carried out by a trained service engineer. The check on the cables K takes place at the same time as the EKG measurement and defects D can be detected quickly and easily by any operator of the EKG device. Moreover, if different currents are impressed on the useful signal paths, it is also possible to determine which useful signal path has a signal path defect.

If the checked currents impressed on the useful signal paths 6*a*, 6*b* are within the measuring range and, for example, two connected electrodes have been detected and the current measurement on the first interference signal path also measures the currents that were coupled into the first interference signal path via two electrodes, both electrodes are applied and there is no signal path defect. This can also be additionally or alternatively established if none of the impressed currents flows on the shield.

If the checked currents which have been impressed on the useful signal paths 6a, 6b are within the measuring range and, for example, two connected electrodes have been detected, but the current measurement on the first interference signal path, for example, only measures one current that was coupled onto the interference signal path via an electrode, there is a signal path defect in a useful signal path. However, then the current of the defective useful signal path is discharged via the shield and can alternatively or additionally be detected there.

Figure 6:
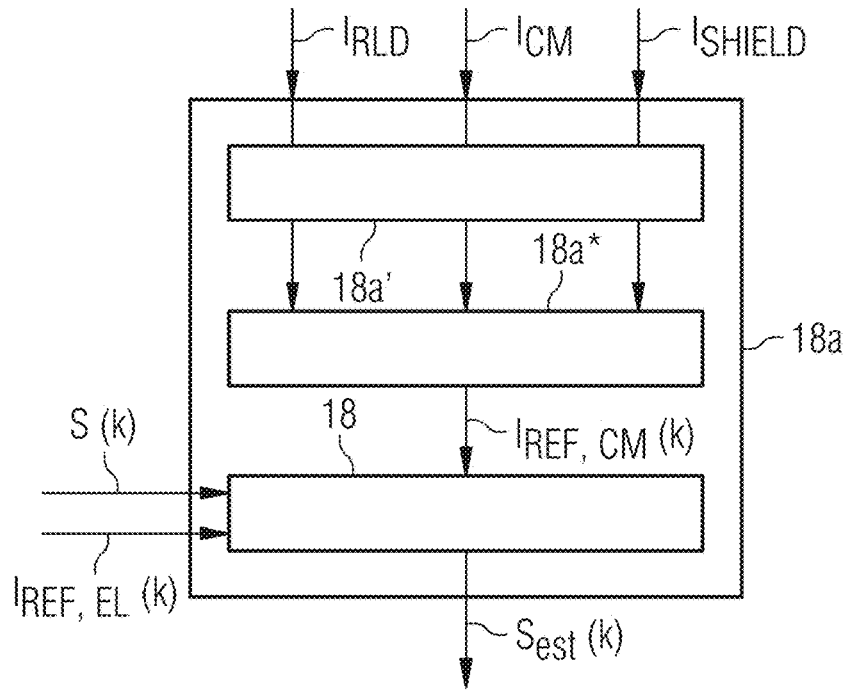
Figure 7:
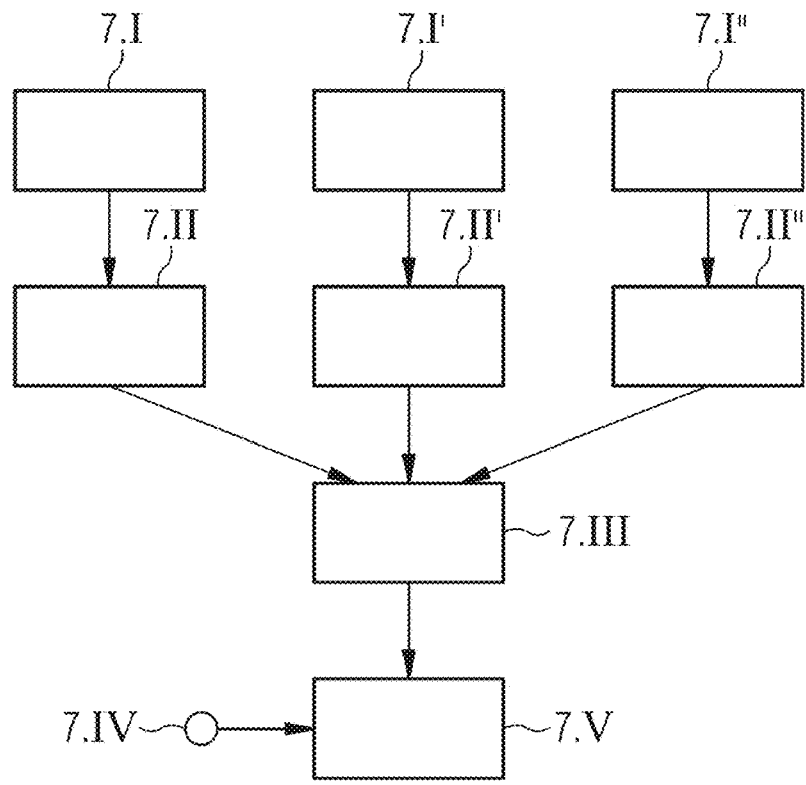

FIG. 6 and FIG. 7 are described jointly in the following. Herein, FIG. 6 shows an example embodiment of an interference signal evaluation unit 18a. Such an interference signal evaluation unit 18a determines both interferences that occur and a measurement signal $S_{est}(k)$ that has been freed of interference. FIG. 7 is a schematic depiction as a block diagram of an example embodiment of a method according to the invention for detecting interferences and for determining a measurement signal $S_{est}(k)$ that has been freed of interferences. In steps 7.I, 7.I', 7.I", the interference signal evaluation unit 18a in each case receives as input signals the interference signals $I_{RLD}$, $I_{CM}$, $I_{SHIELD}$ previously detected in the interference signal detection units 17, 21, 55.

In an interference signal-determining unit 18a' of the interference signal evaluation unit 18a, interference signals with a frequency in the range of a mains frequency are extracted from these simple measurement signals. This takes place in step 7.II for the first interference signal $I_{RLD}$, in step 7.II' for the second interference signal $I_{CM}$ and step 7.II" for the third interference signal $I_{SHIELD}$, in each case for example by way of a frequency analysis.

In step 7.III, the signals defined in this way as one frequency are combined in a combination unit 18a* of the interference signal evaluation unit 18a to form one combination signal corresponding to the reference interference signal $I_{Ref,CM}(k)$ already described in respect of FIG. 2 to FIG. 5. This process can, for example, take place by way of weighted addition or subtraction of the signals. Herein, weighting can be varied as required, i.e. for example according to the strength of the respective couplings-in or interference fields.

In a step 7.IV, bioelectric measurement signals S(k) that were previously determined by the signal measuring circuit 2 are received by the interference signal evaluation unit 18a.

The interference signal evaluation unit 18a furthermore comprises an interference signal suppressing unit 18. This serves to reduce the interference signal components based on the reference interference signal $I_{Ref,CM}(k)$ determined. In addition, the interference signal suppressing unit 18 also receives a reference interference signal $I_{Ref,E1}(k)$ generated by the interference field measuring circuit 60 which is also used to reduce the interference effects. The precise function of the interference signal suppressing unit 18 is illustrated in FIG. 3 and FIG. 4. The generation of a low-interference signal $S_{est}(k)$ takes place in step 7.V in the manner illustrated in FIG. 4.

Alternatively, however, it is also possible to use a plurality of further algorithms, such as, for example, pattern recognition or a Kalman filter to evaluate the reference interference signals $I_{Ref,CM}(k)$, $I_{Ref,E1}(k)$.

In conclusion, reference is made once again to the fact that the apparatuses and method described in detail above are only example embodiments which can be modified by the person skilled in the art in a wide variety of ways without departing from the scope of the invention. For example, the differential voltage measuring system does not necessarily have to be an EKG device, it could also be another medical device with which bioelectric signals are detected such as, for example, an EEG, EMG etc. Furthermore, the use of the indefinite article "a" or "an" does not preclude the possibility of the features in question also being present on a multiple basis. Similarly, the term "unit" does not preclude the possibility of this consisting of a plurality of components which could optionally also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An interference signal measuring facility for a differential voltage measuring system including a signal measuring circuit for measuring bioelectric signals with a number of useful signal paths, each of the useful signal paths respectively including a sensor electrode, the interference signal measuring facility comprising:
   a plurality of additional sensor leads, each additional sensor lead of the plurality of additional sensor leads corresponding with a respective sensor electrode and electrically connected to a ground connection of a supply lead of the respective sensor electrode; and
   a plurality of measuring amplifier circuits, each measuring amplifier circuit of the plurality of measuring amplifier circuits
      respectively corresponding to each respective sensor electrode,
      including a first input terminal electrically connected to a shield of a respective supply lead of a respective sensor electrode via an electrical resistor and a second input terminal electrically connected to a common ground connection, wherein the second input terminal is not connected to the shield of the respective supply lead except for internal connections of the respective measuring amplifier circuit, and configured to detect a change in electric potential occurring on the respective sensor lead, and determine an electrode reference interference signal from the detected change in electric potential.

2. The interference signal measuring facility of claim 1, wherein each measuring amplifier circuit of the plurality of measuring amplifier circuits includes a respective programmable amplifier circuit.

3. An interference signal compensation facility, comprising:

the interference signal measuring facility of claim 1; and an evaluation unit including a first adaptive filter configured to generate a first interference-reduced measurement signal based on a measurement signal and a reference common-mode interference signal, a second adaptive filter configured to generate an adapted reference electrode interference signal reduced by common-mode interferences based on the electrode reference interference signal and the reference common-mode interference signal, and a third adaptive filter downstream of the first adaptive filter and the second adaptive filter, the third adaptive filter configured to determine a second interference-reduced measurement signal based on the first interference-reduced measurement signal and the adapted reference electrode interference signal.

4. A differential voltage measuring system, comprising:

at least one first electrode and one second electrode configured to measure bioelectric measurement signals;

at least one third electrode configured to equalize a potential between a measurement object and the differential voltage measuring system; and a measuring facility including a signal measuring circuit configured to measure the bioelectric signals, a reference-signal unit configured to detect a first interference signal, and the interference signal measuring facility of claim 1.

5. The differential voltage measuring system of claim 4, wherein the measuring facility includes a detection apparatus configured to detect interferences on signal paths in the differential voltage measuring system, the differential voltage measuring system including:

at least one analysis unit connected to at least one shield of a respective supply lead, the at least one analysis unit configured to detect interference in a useful signal path of the differential voltage measuring system via a signal measured in response to interference on a shield of the useful signal paths.

6. The differential voltage measuring system of claim 4, wherein the measuring facility includes a detection apparatus comprising:

at least one first current application unit configured to impress a signal on a first useful signal path, and a defect analysis unit configured to detect a signal path defect in a second useful signal path of the differential voltage measuring system via a previously impressed signal measured in response to detecting interference on at least one shield.

7. The differential voltage measuring system of claim 6, wherein the at least one first current application unit is configured to impress respectively different signals onto respectively different useful signal paths.

8. The differential voltage measuring system of claim 7 including at least one first comparator configured to determine whether a signal of a useful signal path is within a measuring range.

9. The differential voltage measuring system of claim 7, including a second interference signal path for measuring a second interference signal.

10. The differential voltage measuring system of claim 9, including an interference signal evaluation unit configured to measure a third interference signal on the at least one shield.

11. The differential voltage measuring system of claim 10, wherein the interference signal evaluation unit is configured to form a combination signal of at least two of the first interference signal, the second interference signal or the third interference signal.

12. A method for generating an interference-reduced biological measurement signal, the method comprising:

detecting a possibly interference-afflicted measurement signal;

detecting an electrode reference interference signal via a measuring amplifier circuit, for each sensor electrode of a plurality of sensor electrodes, the measuring amplifier circuit including a first input terminal being electrically connected to a shield of a respective supply lead of a respective sensor electrode via an electrical resistor and a second input terminal being electrically connected to a common ground connection, the second input terminal not being connected to the shield of the respective supply lead except for internal connections of the respective measuring amplifier circuit, the measuring amplifier circuit being configured to detect a change in electric potential occurring on a respective sensor lead of the respective sensor electrode and configured to determine the electrode reference interference signal from the change in electric potential detected;

detecting a reference common-mode-interference signal;

generating a first interference-reduced measurement signal based on a measurement signal and the reference common-mode interference signal;

generating an adapted reference electrode interference signal, reduced by common-mode interferences based on the electrode reference interference signal determined by the interference signal measuring facility and the reference common-mode interference signal; and generating a second interference-reduced measurement signal based on the first interference-reduced measurement signal and the adapted reference electrode interference signal.

13. A non-transitory computer program product storing a computer program, directly loadable into a storage facility of a voltage measuring system, including program sections for executing the method of claim 12 when the computer program is executed in the voltage measuring system.

14. A non-transitory computer-readable medium storing program sections, readable and executable by a computing unit, to execute the method of claim 12 when the program sections are executed by the computing unit.

15. A differential voltage measuring system, comprising:

at least one first electrode and one second electrode configured to measure bioelectric measurement signals;

at least one third electrode configured to equalize a potential between a measurement object and the differential voltage measuring system; and a measuring facility including
- a signal measuring circuit configured to measure the bioelectric signals,
- a reference-signal unit configured to detect a reference common-mode interference signal, and
- the interference signal measuring facility of claim 2.

16. An interference signal compensation facility, comprising:

the interference signal measuring facility of claim 2; and
an evaluation unit including
- a first adaptive filter configured to generate a first interference-reduced measurement signal based on a measurement signal and a reference common-mode interference signal,
- a second adaptive filter configured to generate an adapted reference electrode interference signal reduced by common-mode interferences based on the electrode reference interference signal and the reference common-mode interference signal, and
- a third adaptive filter downstream of the first adaptive filter and the second adaptive filter, the third adaptive filter configured to determine a second interference-reduced measurement signal based on the first interference-reduced measurement signal and the adapted reference electrode interference signal.

17. The differential voltage measuring system of claim 5, wherein the detection apparatus includes:
- at least one first current application unit configured to impress a signal on a first useful signal path, and
- a defect analysis unit configured to detect a signal path defect in a second useful signal path of the differential voltage measuring system via a previously impressed signal measured in response to detecting interference on the at least one shield.

18. The interference signal measuring facility of claim 1, wherein the first input terminal and the second input terminal have no connection to one another except for the internal connections of the respective measuring amplifier circuit.

19. The interference signal measuring facility of claim 1, wherein the second input terminal is directly connected to the common ground connection.

* * * * *